United States Patent [19]
Greco et al.

[11] 4,442,133
[45] Apr. 10, 1984

[54] ANTIBIOTIC BONDING OF VASCULAR PROSTHESES AND OTHER IMPLANTS

[76] Inventors: Ralph S. Greco, 29 Goltra Dr., Basking Ridge, N.J. 07920; Richard A. Harvey, 1 Overland Rd., East Brunswick, N.J. 08816

[21] Appl. No.: 351,324

[22] Filed: Feb. 22, 1982

[51] Int. Cl.$^3$ ............................ A61F 1/00; A61F 1/24
[52] U.S. Cl. ................................................. 427/2; 3/1; 3/1.4; 128/334 R
[58] Field of Search ...................... 3/1, 1.4; 128/334 R, 128/; 427/2

[56] References Cited

U.S. PATENT DOCUMENTS

| | | | |
|---|---|---|---|
| 3,425,418 | 2/1969 | Chvapil et al. | 128/334 R |
| 3,520,949 | 7/1970 | Shepherd et al. | 3/1.4 X |
| 4,116,898 | 9/1978 | Dudley et al. | 3/1.4 X |
| 4,302,368 | 11/1981 | Dudley et al. | 3/1 X |

Primary Examiner—Ronald L. Frinks
Attorney, Agent, or Firm—Robert A. Green

[57] ABSTRACT

A method of preparing a surgical vascular graft wherein a length of graft material carries an absorbed coating of tridodecyl methyl ammonium chloride (TDMAC) surfactant and an antibiotic bound thereto. A length of graft material such as polytetrafluoroethylene or Dacron is soaked in a 5% by weight solution of TDMAC for 30 minutes at room temperature, air dried and then washed in distilled water to remove excess TDMAC. The graft carrying the absorbed cationic TDMAC surfactant coating is incubated in a solution of negatively charged antibiotic for one hour, washed in sterile water to remove unbound antibiotic and stored for use in the operating room.

3 Claims, 2 Drawing Figures

ANTIBIOTIC BONDING OF VASCULAR PROSTHESES AND OTHER IMPLANTS

BACKGROUND OF THE INVENTION

At the present time, vascular grafts are used to replace diseased blood vessels as well as for vascular access in patients with renal failure and those receiving chemotherapy. In surgical procedure, the graft is usually made of polytetrafluoroethylene or DACRON synthetic fiber of polyethylene terephthalate. Vascular prosthetic infections occur as complications of arterial reconstructive surgery, and though the infection rate is small due to the use of systemic antibiotics, it would be desirable to reduce the rate of infection to zero. Presently, the accepted treatment of graft infection consists of removal of the graft, ligation of the host vessel, extra-anatomic bypass, and massive doses of systemic antibiotics. Unfortunately, even this aggressive treatment is not completely successful due to the inability of antibiotics to penetrate the graft matrix that harbors the bacteria. Also, the clinical manifestations of infection become apparent after the infection is well established. Finally, thrombosis and suture-line disruption are not amenable to antibiotic therapy. These morbid results with established vascular prosthetic infection make complete eradication mandatory.

SUMMARY OF THE INVENTION

Briefly, the invention comprises coating vascular prostheses with the cationic surfactant, tridodecyl methyl ammonium chloride (TDMAC), and then, prior to operation, bonding the antibiotic to the surfactant coated prosthesis.

DESCRIPTION OF THE INVENTION

In practicing the invention, grafts of polytetrafluoroethylene or Dacron are cut into 0.5 cm segments and soaked in a solution of 5% by weight of tridodecyl methyl ammonium chloride (TDMAC) in ethanol. TDMAC is a cationic surfactant. This soaking operation is carried out for thirty minutes at room temperature. Next, the grafts are air dried and thoroughly washed in distilled water to remove excess TDMAC. The grafts carrying an adsorbed coating of TDMAC are then incubated in a solution of a negatively charged antibiotic such as penicillin, oxacillin, ticarcillin, carbenicillin, the cephalosporins or cefoxitin for one hour. The antibiotic-TDMAC bound grafts are then again thoroughly washed in sterile water to remove unbound antibiotic. Grafts are then stored for use in the operating room.

It is noted that the above-described procedure is also operable with grafts of Dacron or other materials which will accept the surface-treating procedure. It is also noted that the coupling of the surfactant and antibiotic is non-covalent bonding so that the antibiotic is available to perform its antibacterial function in the body.

In vitro and in vivo animal studies demonstrate that grafts treated according to the invention exhibit superior antibacterial activity to control grafts and grafts simply treated with antibiotic or surfactant alone. In the accompanying figures, the results of in vitro experiments utilizing radiolabeled cefoxitin demonstrate that TDMAC bonded grafts exhibit superior antibacterial activity against Staphylococcus aureus and greater concentrations by liquid scintillation counting when compared to grafts bound with another surfactant (benzalkonium chloride) and grafts simply soaked in the antibiotic. In in vivo experiments conducted in the rat, grafts bound to cefoxitin with TDMAC exhibit far greater concentrations of antibiotic which persist for up to ten days after implantation.

Figure 1:
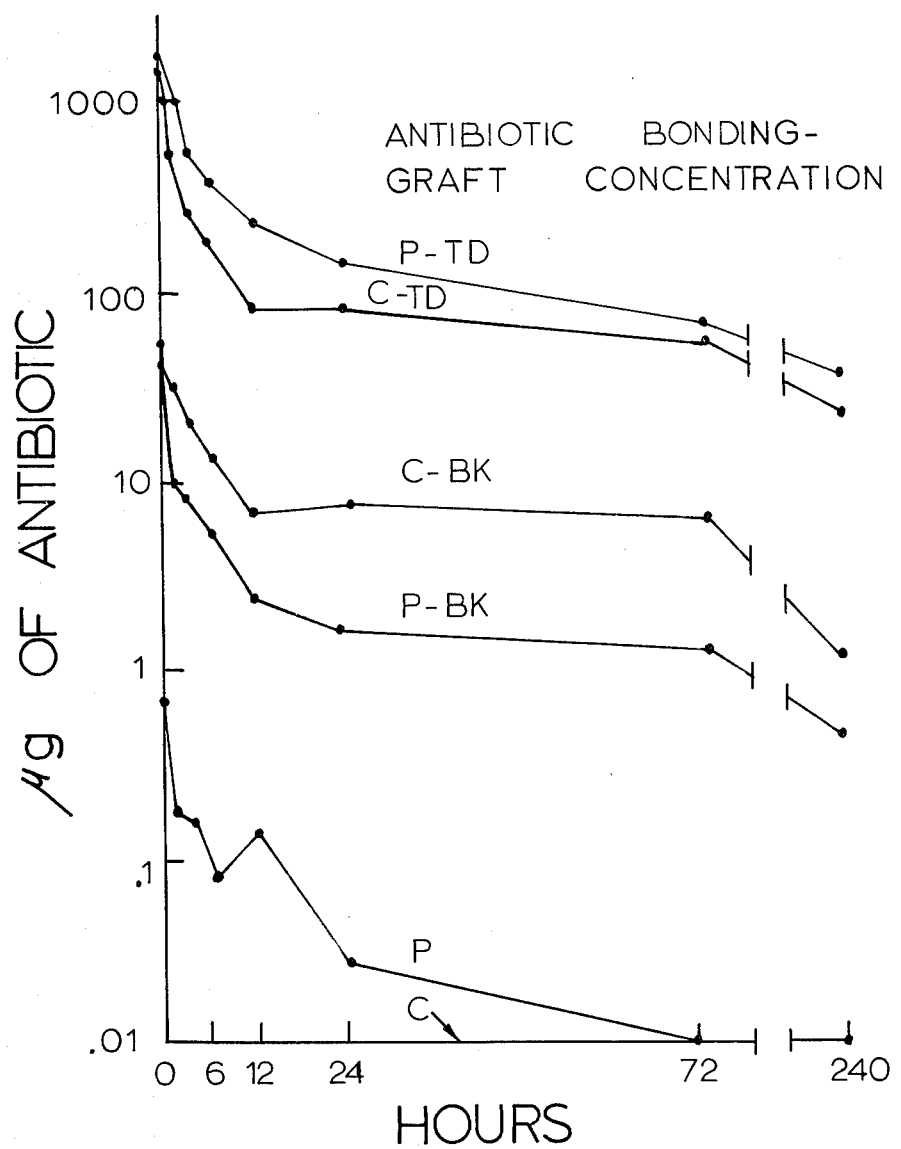
FIG. 1 shows curves which compare the persistence of antibiotics of various types on grafts.

In the results of the tests of the invention shown in FIG. 1, the following abbreviations are utilized: C-TD=cefoxitin-TDMAC; P-TD=penicillin-TDMAC; C-BK=cefoxitin-benzalkonium; P-BK=penicillin-benzalkonium; P=penicillin soaked; C=cefoxitin soaked. All grafts utilized were polytetrafluoroethylene (Gore-TEX). In the tests performed, grafts were bound or soaked in $^{14}$C-cefoxitin or $^{14}$C-penicillin. Grafts were then placed in a muscular pouch in the medial aspect of the thigh of Sprague-Dawley rats. Grafts were harvested at various time intervals up to 10 days after implantation and the amount of antibiotic remaining on the graft was measured by liquid scintillation counting. The data of FIG. 1 show that TDMAC binds more than ten times as much cefoxitin and penicillin as benzalkonium and more than a thousand times as much antibiotic as soaking the graft in cefoxitin or penicillin. This activity persists for up to 10 days after implantation and demonstrates that antibiotic bonding is efficacious in vivo as well as in vitro. Finally, both singly charged anionic antibiotics (cefoxitin and penicillin) behave similarly with TDMAC, and this indicates that the bonding process is non-covalent.

Figure 2:
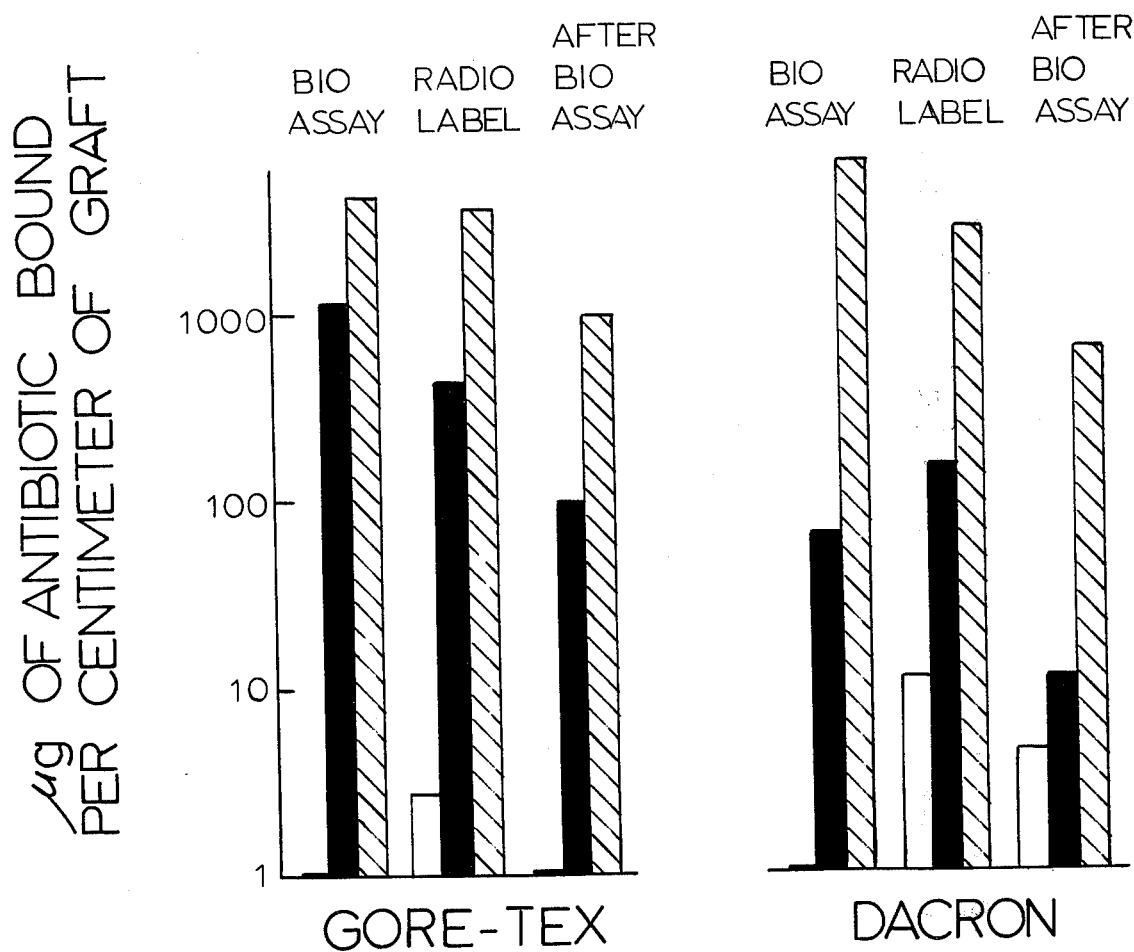
FIG. 2 is a bar graph showing the efficacy of the invention over the prior art.

In addition, FIG. 2 illustrates the efficacy of the invention as compared to the prior art. In the tests which produced the graphs of FIG. 2, $^{14}$C-cefoxitin, a negatively charged antibiotic, is bound to polytetrafluoroethylene (Gore-Tex) grafts and Dacron grafts. Grafts soaked in 10 mg of cefoxitin are compared to grafts bound to 10 mg of cefoxitin with benzalkonium chloride and bound to 10 mg of cefoxitin with TDMAC. In each study, a bioassay is shown in which the concentration of antibiotic is measured by zones of inhibition against Staphylococcus aureus. Also, a radiolabeled determination of $^{14}$C-cefoxitin by liquid scintillation counting is also provided. Finally, the amount of antibiotic remaining after completion of the bioassay by liquid scintillation counting is likewise shown. As can be seen with both vascular grafts, Gore-Tex and Dacron, TDMAC binds far greater concentrations of $^{14}$C-cefoxitin than does benzalkonium, and both bonded surfaces exhibit greater antibacterial activity and/or concentration of antibiotic then grafts simply soaked in the antibiotic.

Therefore, these studies demonstrate that antibiotic bonding with TDMAC is far superior to treating grafts with antibiotic only or with benzalkonium bonding. In addition, this is true with bore Gore-Tex and Dacron, and, finally, the amount of antibiotic measured in the bioassay is virtually identical to that measured by liquid scintillation counting demonstrating that the biological activity of the antibiotic is unaltered by the binding process.

The theory of operation of the invention will now be described: A number of studies in the laboratory have shown that the surfactant, benzalkonium chloride adsorbs to the surface of polytetrafluoroethylene grafts and can serve as a cationic anchor for the binding of negatively charged antibiotics. Since the binding of benzalkonium occurs through interaction of the alkyl side chain of the surfactant with the hydrophobic surface of the graft, the use of a quarternary ammonium salt with three hydrophobic side chains, rather than one, further stabilizes surfactant binding. Tridodecyl methyl ammonium chloride is selected since it has such a hydrophobic side chain. TDMAC treated grafts bind more antibiotic and exhibit better retention of the antibiotic in the presence of serum than control grafts or benzalkonium treated grafts. This is due in part to the fact that polytetrafluoroethylene grafts show a higher affinity and greater binding capacity for TDMAC compared with the more weakly lipophilic surfactant, benzalkonium chloride. However, dissociation of the antibiotic primarily reflects disruption of the interaction between antibiotic and surfactant rather than the release of the surfactant from the surface of the graft. Thus, TDMAC in addition to binding more firmly to the surface of the graft, provides a cationic anchor which is qualitatively different from that of other surfactants.

What is claimed is:

1. The method of preparing a vascular graft comprising the steps of preparing a length of a graft material, soaking said length of graft material in a solution of about 5% by weight of tridodecyl methyl ammonium chloride in ethanol for about 30 minutes at room temperature, washing said graft in distilled water to remove excess tridodecyl methyl ammonium chloride but leaving an adsorbed coating thereon, incubating, for about one hour, the graft carrying the adsorbed coating of tridodecyl methyl ammonium chloride in a solution of antibiotic selected from the group consisting of penicillin, oxacillin, ticarcillin, carbenicillin, the cephalosporins, and cefoxitin, washing the graft in sterile water to remove unbound antibiotic, and storing the graft for use in the operating room.

2. The method defined by claim 1 wherein said graft material is polytetrafluoroethylene.

3. The method defined in claim 1 wherein said graft material is polyethylene teraphthalate.

* * * * *